(12) United States Patent
Seiler et al.

(10) Patent No.: US 6,287,296 B1
(45) Date of Patent: *Sep. 11, 2001

(54) DEVICE FOR THE REMOVAL OF TISSUE FROM THE CORNEA OF AN EYE

(75) Inventors: Theodor Seiler, Dresden; Andreas Borrmann, Ingelheim, both of (DE)

(73) Assignee: Herbert Schwind GmbH & Co. KG, Kleinostheim (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/571,798

(22) Filed: Dec. 13, 1995

(30) Foreign Application Priority Data

Nov. 30, 1995 (EP) .................................................. 95118889

(51) Int. Cl.⁷ ...................................................... A61B 18/09
(52) U.S. Cl. ................................. 606/5; 606/3; 606/10; 606/13
(58) Field of Search ........................................... 606/2–19

(56) References Cited

U.S. PATENT DOCUMENTS

| | | | |
|---|---|---|---|
| 4,729,372 | * | 3/1988 | L'Esperance ............................ 606/5 |
| 4,784,135 | | 11/1988 | Blum et al. . |
| 4,838,266 | | 6/1989 | Koziol et al. . |
| 4,911,711 | * | 3/1990 | Telfain et al. ........................... 606/5 |
| 4,953,969 | | 9/1990 | Fedorov . |
| 4,988,348 | | 1/1991 | Bille . |
| 5,090,798 | | 2/1992 | Kohayakawa . |
| 5,163,934 | * | 11/1992 | Munnerlyn ............................... 606/3 |
| 5,284,477 | * | 2/1994 | Hanna et al. ........................... 606/12 |
| 5,445,633 | | 8/1995 | Nakamura et al. . |

FOREIGN PATENT DOCUMENTS 651 082A1  5/1995 (EP) .

OTHER PUBLICATIONS

S.L. Trokel et al. "Excimer Laser Surgery of the Cornea", Americal Journal of Ophthalmology, 96:710–715, Dec. 1983.

* cited by examiner

Primary Examiner—David M. Shay
(74) Attorney, Agent, or Firm—Crowell & Moring, LLP

(57) ABSTRACT

Device for the removal of tissue from the cornea of an eye using a laser beam generator for the production of a laser beam, an optical device by which, during the removal of the tissue, the laser beam is directed onto the cornea to be treated, with an approximately circular beam cross section and a defined removal profile for the beam energy that is transferred to the corneal tissue to be removed, and a control device for controlling the optical device so that a removal profile is formed that, in the radial section starting out from the central beam axis 2 of the beam cross section, has an approximately spherical or concave course in an internal radial region 3 that changes into a point of inflection 4 and an outer radial region 5 that joins the point of inflection 4, with a convex or monotonic decreasing course.

14 Claims, 5 Drawing Sheets

DEVICE FOR THE REMOVAL OF TISSUE FROM THE CORNEA OF AN EYE

FIELD OF THE INVENTION

The invention concerns a device for the removal of tissue from the cornea of an eye using a laser beam generator for the production of a laser beam, including an optical device by means of which, during the removal of the tissue, the laser beam is directed onto the cornea to be treated, with a beam cross section and a defined removal profile for the beam energy that is transferred to the corneal tissue to be removed, and a control device for controlling the optical device.

BACKGROUND OF THE INVENTION

Such a device is known from DE 4,103,615 C2. The device serves in the removal of deficient vision that results, in particular, as a consequence of a refraction anomaly in the eye. Thereby, a laser beam is directed onto the cornea, which has a removal profile over its cross section, i.e., its beam cross section has a beam energy profile that is to be transferred to the corneal tissue. Previously known surgical treatment devices are problematic, especially for myopia correction with high vertex power, especially over six diopters, in that the cornea has to be treated using a relatively high depth of removal in order to obtain adequate correction of the refraction anomaly. A risk of scar formation in the postoperative healing process hereby arises, especially at the edge of the field removed. A scar adversely influences vision, especially in the case of an enlarged pupil aperture with bad illumination or subdued light or, at night.

SUMMARY OF THE INVENTION

The object of the invention is to generate a device of the type designated at the beginning in which a considerable reduction in the depth of removal is achieved during the correction of a refraction anomaly, especially myopia.

According to the invention, this object is accomplished in that the radial section, starting out from the central beam axis of the beam cross section, the removal profile formed by the optical device, has an approximately spherical or concave course in an inner radial region that changes into a point of inflection and an outer radial region that joins the point of inflection, with a convex or, monotonic decreasing course.

A considerable reduction in the depth of removal is achieved as a result of the removal profile that is formed in this way for the beam energy within the beam cross section that is transferred by the laser beam to the corneal tissue that is to be removed.

Starting out from the central axis of the beam, the point of inflection of the removal profile lies at approximately 40–60% or, especially, approximately 50% of the respective radial dimension of the beam cross section.

In a preferred way, the optical device in which the removal profile is set up is charged by a laser beam that has a constant intensity distribution over its beam cross section. In order to produce a constant intensity distribution, use can be made, for example, of a beam integrator in the form known from DE 4,103,615 C2.

One achieves a reduction in the depth of removal of approximately 30% relative to the approximately spherically formed removal profiles that are known. Thereby, the danger of scar formation is considerably reduced, especially in the edge region, and removal diameters between 6 and 8 mm can be implemented during corneal transfer.

The beam cross section can be circular, approximately circular and, for astigmatism correction, oval or approximately elliptical.

In order to achieve the desired removal profile, a diaphragm device can be used that simultaneously forms several beam spots on the tissue surface to be treated. These beam spots can be circular and can have differing diameters. In addition, it is possible to utilize beam spots with a regular shape, e.g., a polygonal shape (e.g. hexagonal, octagonal), or those with an irregular geometry that has been assembled, for example, from fractals. The beam spots or spot that are/is formed in this way can produce the desired structuring of the corneal tissue with the removal profile according to the invention by rotation of the diaphragm aperture or rotation of the beam spot that is formed on the tissue. Such a device is known from EPO 651,982 A1. The wavelength of the laser beam to be used lies in the short wave ultraviolet region (EP-A-0,111,080 or Trokel et al., Excimer Laser Surgery of the Cornea, American Journal of Ophthalmology 96:710–715, December 1983).

It is also possible to form a beam spot that is guided over the tissue surface to be treated. In this connection, a laser beam is, in essence, guided over the tissue surface to be treated, especially the stroma, using the means that are present in the case of the known device, whereby the laser beam forms a beam spot on the tissue surface with a fraction of the surface dimension of the tissue surface to be treated. The surface dimension of the beam spot amounts to approximately $1/30$ to $1/10$ that of the tissue surface to be treated. In addition, the beam spot formed on the tissue to be treated has a regular polygonal or an irregular geometrical shape, especially at its edge. This irregular geometrical shape can be formed from several round spots of differing diameter in an irregular arrangement that are formed simultaneously or by a spot that is, in particular, star-shaped with uneven lines limiting the edges of the aperture or a spot with irregular ramifications that are formed by fractal geometry elements according to the mathematical theory based on the work of B. Mandelbrot, Les objets fractals [Fractal objects], Flammarion Publishers, Paris, 1974–1984, and The fractal geometry of nature, W. H. Freeman and Company, San Francisco, 1977–1982. In order to obtain this geometrical shape of the beam spot that is formed on the tissue surface, the region of the aperture in the diaphragm device has to be correspondingly constructed. For this purpose, several circular apertures can be provided in the form shown in EP0,651,982 A1, or a diaphragm aperture can be provided that exhibits ramifications and branches at its edge or is constructed in an irregular star shape.

This beam spot that has been formed and rotated in this way is guided over the tissue surface to be treated, with the help of a deflection device. It is certainly known from EPO 151,869 A1 that one can form a beam spot on the tissue surface to be treated with the laser beam supplied by the laser beam source and that, with this, one can scan the tissue region to be treated. However, use is not made of a diaphragm with which the beam spot is brought into an irregular geometrical shape, especially a geometrical shape that is formed by fractal geometry elements.

During beam, i.e., especially in the form of pulses, the beam spot is rotated about its center (axis). This can take place by rotating the laser beam that exits from the diaphragm with the help of one or more prisms or mirrors. Rotation can be achieved without additional expense by rotating the diaphragm aperture. One or more, especially, two to ten beam pulses can be produced in each scanning or deflection position. Deflection or scanning of the beam spot takes place relative to a fixed line that is formed by, for example, a fixed laser (EPO 651,982 A1), whereby the eye that is to be treated is aligned with its line of vision along the fixed line. In this way, deflection can take place in planes that are oriented vertically to the fixed line according to the X and Y coordinates or by swivelling the laser beam directed onto the corneal tissue with respect to the fixed line.

In the device according to the invention, use can be made of a laser beam source with a reduced laser output level. As a result of the beam geometry that is irregular, especially at the edge of the diaphragm aperture region and formed especially by fractal geometry elements, virtually all types of vision corrections can be achieved with the help of, in particular, a regular or irregular star-shaped diaphragm aperture, especially a fractal edge configuration. Especially astigmatism corrections and, above all, irregular astigmatisms can be corrected. Relative to an untreated surface, one achieves a flattened course of the surface to be treated in the treatment area of the laser beam.

The device can be used not only for the removal of corneal tissue at the exterior of the cornea but also for the removal of tissue in the stroma.

BRIEF DESCRIPTION OF THE DRAWINGS

The figures serve for further explanation of the invention. They show.

DETAILED DESCRIPTION OF THE PREFERRED EMBODIMENTS

Figure 1:
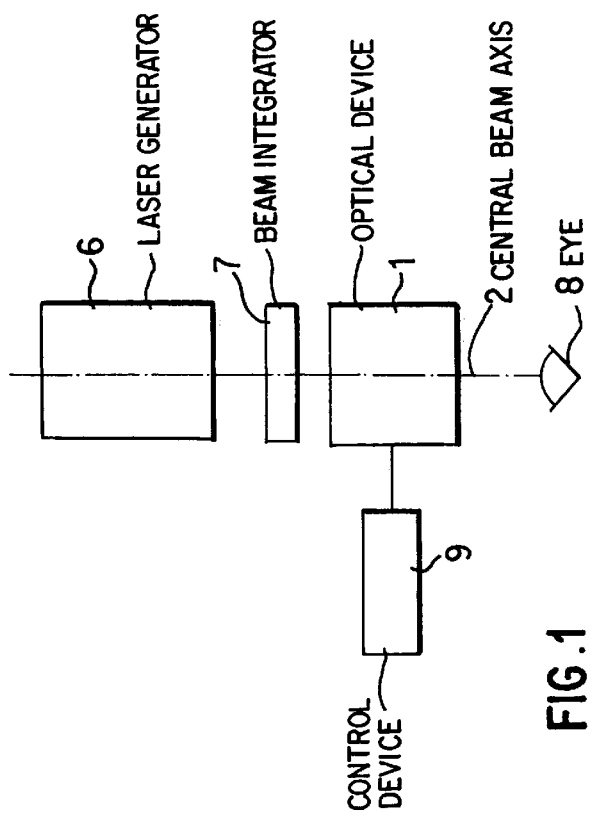
FIG. 1: a diagrammatic embodiment example of the invention.

FIG. 1 represents an embodiment example that has a laser beam source in the form, for example, of an excimer laser that emits a laser beam at a wavelength of, in particular, 193 nm so that the corneal tissue to be removed is decomposed and removed. Wavelengths of 199 nm and 208 nm are also suitable. This laser beam source forms a laser generator 6. The beam from the laser generator 6 is homogenized with the help of a beam integrator 7 so that an essentially constant intensity distribution is produced over the beam cross section that is initiated in an optical device 1. The beam integrator can be constructed in the way known from DE 4,103,615 C2.

Figure 2:
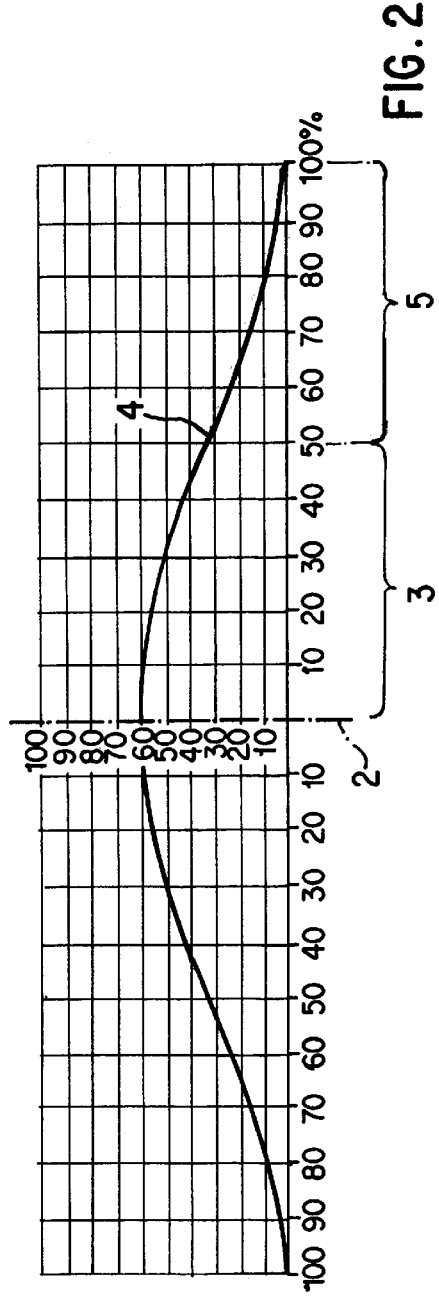
FIG. 2: a removal profile for the laser beam directed onto the eye to be treated.

The optical device 1 which is found in the beam path with a homogeneous distribution of intensity in the beam cross section, produces a removal profile so represented in FIG. 2 in the radial section through the central beam axis 2. Thereby, optical device 1 can have an exposure system with which in the respective radial regions of the beam cross section which form the treatment cross section at the cornea of an eye 8 to be treated, differing exposure times with the homogeneous laser beam are set up. The profile of the beam energy that is transferred from the beam to the corneal tissue to be removed, represented in FIG. 2, has a corresponding exposure time profile. This removal profile corresponds, respectively, to the radial sections through the central beam axis 2 of the treatment laser beam that emerges from optical device 1 and that is incident on the cornea of the eye 8 to be treated.

Over the beam cross section, changing beam energy to be transferred for different radius regions (removal profile) can be attained for the achievement of corresponding exposure times in the radial regions respectively by changing diaphragm apertures in the homogeneous beam cross section, optionally in connection with a lens system, e.g., a zoom lens system. Such a device is known, for example, from DE 4,103,615 C2.

However, instead of controlling the exposure time, it is also possible to provide the laser beam with a homogeneous intensity distribution over its beam cross section by means of a filter with which an intensity profile is produced that corresponds to the removal profile of FIG. 2.

To set up the corresponding intensity profile or the exposure time profile for the achievement of the removal profile represented in FIG. 2, optical device 1 can be linked to a control device 9 that has an electronic processing device. The required data for the correction of the refraction anomaly, for example, the corresponding vertex power of the radius of the treatment cross section (beam cross section) are entered into the control device 9. The control device also has a memory in which the removal profile of FIG. 2 is stored. This removal profile is then used together with the data that have been entered, respectively, for the refraction correction in order to control the optical device 1.

FIG. 2 shows a radial section through a removal profile about the central beam axis 2. The beam energy to be transferred to the corneal tissue to be removed is plotted on the coordinate. This beam energy produces the desired removal depths in the corresponding radial regions of the beam cross section. The radius, respectively, of the beam cross section is plotted in percentage data on the abscissa. To that extent, the radial section profile can be applied, respectively, to the required radii of the beam cross section. The beam cross section can be constructed in an approximately circular shape; however, cross sectional shapes that differ from this can also be used depending on the refraction correction that is to be applied, e.g., oval or approximately elliptical forms, especially in the case of astigmatism correction.

The radial section profile represented in FIG. 2 has an internal radial region 3 with an approximately spherical or concave course starting from the central beam axis 2. This profile curve course goes over to a point of inflection 4. In the embodiment example represented, the point of inflection 4 lies at, for example, 50% of the radius of the beam cross section. At the point of inflection 4, an outer radial region 5 joins a convex or monotonic decreasing course that ends at 100% of the radius of the beam cross section.

Relative to known removal profiles, one achieves an approximately 30% flattening or reduction of the removal depths with equally effective correction of the refraction anomaly, especially with myopia correction. For example, a removal depth of 108 μm was previously required in the center with shortsightedness of 9 diopters. On using a removal profile or a beam energy profile that is transferred to the cornea according to the invention, this removal depth is reduced to 71 μm.

The beam energy profile represented in FIG. 2 can be achieved with, for example, the device represented in FIG.

3. In essence, this has the same components as the device represented in EPO 651,982 A1. The laser beam source 6 emits a laser beam 25 that is led through a beam homogenizer 27 by means of a deflection device that is constructed in the form of a deflecting mirror 26 in the embodiment example represented. The beam homogenizer 27 can be constructed in the way that is known from DE 4,103,615 C2. A uniform beam intensity over the cross section of the beam is produced by means of the beam homogenizer.

Figure 4:
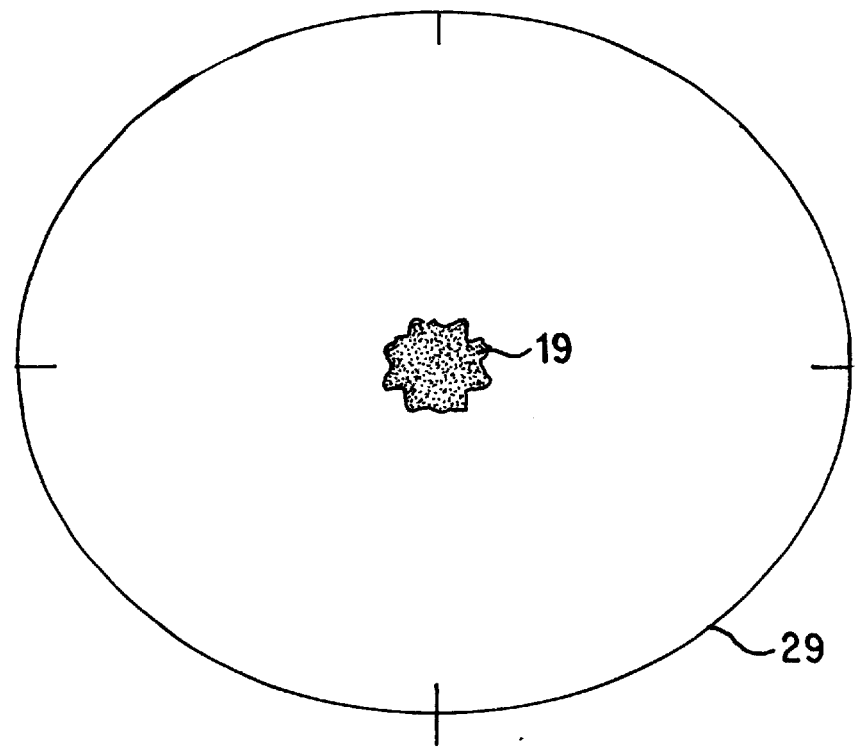
FIG. 4: an embodiment example of an insertable diaphragm.
Figure 5:
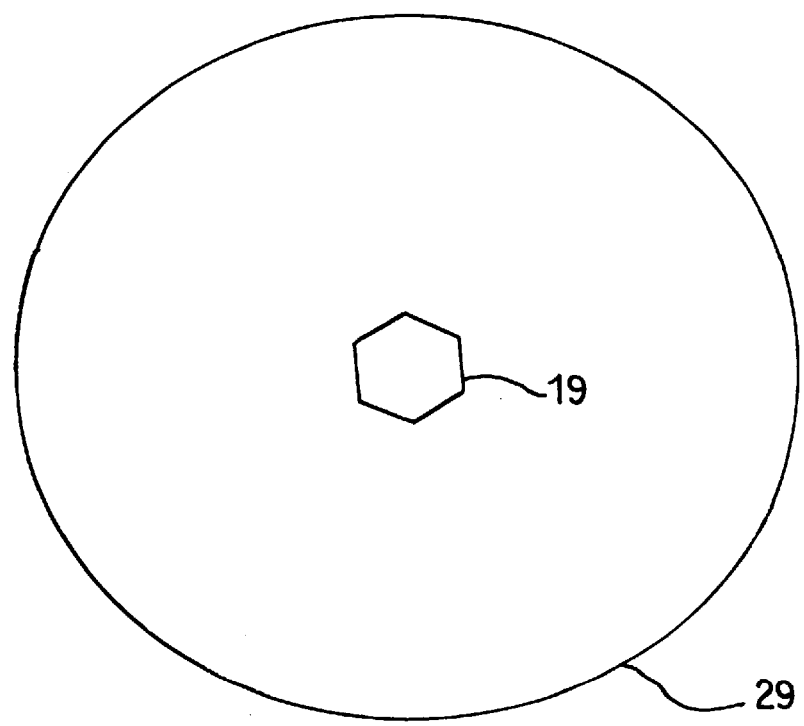
FIG. 5: an additional embodiment of a diaphragm.

A diaphragm device 29 is located in the beam path of the homogenized laser beam with the beam axis 28. The diaphragm device 29 can be constructed in the way that is described in EPO 651,982 A1. Embodiment examples of this diaphragm device 29 are also represented in FIGS. 4 and 5.

The homogeneous laser beam is formed by the diaphragm device 29. The laser beam has a cross section that corresponds to the aperture region of the diaphragm device 29 that is transparent to the laser beam. This shaped laser beam is directed by means of an additional deflection device, which can be constructed in the form of a semitransparent deflection mirror 9, through an objective lens system 20 onto the cornea 14 to be treated of a patient's eye 13. The laser beam source and the optical components provided for the modification and guidance of the laser beam are aligned in a housing 6.

In addition, a fixed target is provided in the form of a fixed laser 17 into which the patient looks with his eye 13 to be treated. The fixed laser 17 forms a fixed line 12. The line of sight of the patient's eye 13 is aligned along this fixed line 12 during treatment. The fixed line 12 is formed by a laser beam from the fixed laser 17. This fixed laser beam forms an image on the surface of the cornea of the eye in the form of a beam spot and the alignment of laser beam 21 for the treatment of the cornea 14 of the eye to be treated takes place with the help of pilot lasers 10 and 11, whereby the laser beam is applied in a suitable form through the diaphragm device 29 and the objective lens system 20. The exact alignment of the laser beam 21 used for the treatment, with fixed line 12, can be observed through oculars 15 and 16.

In addition, a monitoring device 18 is provided, for example, in the form of a monitor, which monitors the course of the treatment. Switching off takes place when the laser beam 21 used for the treatment is no longer aligned with the fixed line 12 in the way that is described in, for example, DE 4,232,021 A1.

As represented in FIG. 4, the diaphragm 29 can have a diaphragm aperture region in the form of an approximately star-shaped diaphragm aperture 19. The star-shaped diaphragm aperture 19 has uneven, curving lines limiting the edges whose geometry is preferably formed by fractal geometry elements. The diaphragm aperture 19 is aligned in the center of the diaphragm 29. The diameter of the diaphragm aperture is approximately 2.2 mm. The beam spot formed on the tissue surface to be treated has a diameter of approximately 1.75 mm. This beam spot has a cross sectional shape that corresponds to the diaphragm aperture 19.

In the embodiment example of a diaphragm aperture represented in FIG. 5, the diaphragm aperture 19 has a regular geometrical shape in the form of a polygon (a hexagon in the embodiment example represented). In regard to the diaphragm aperture, use can also be made of a regular star-shape with edges that run in straight lines. Other polygons, e.g., a square and an octagon, are possible as geometrical shapes for the diaphragm aperture.

Figure 3:
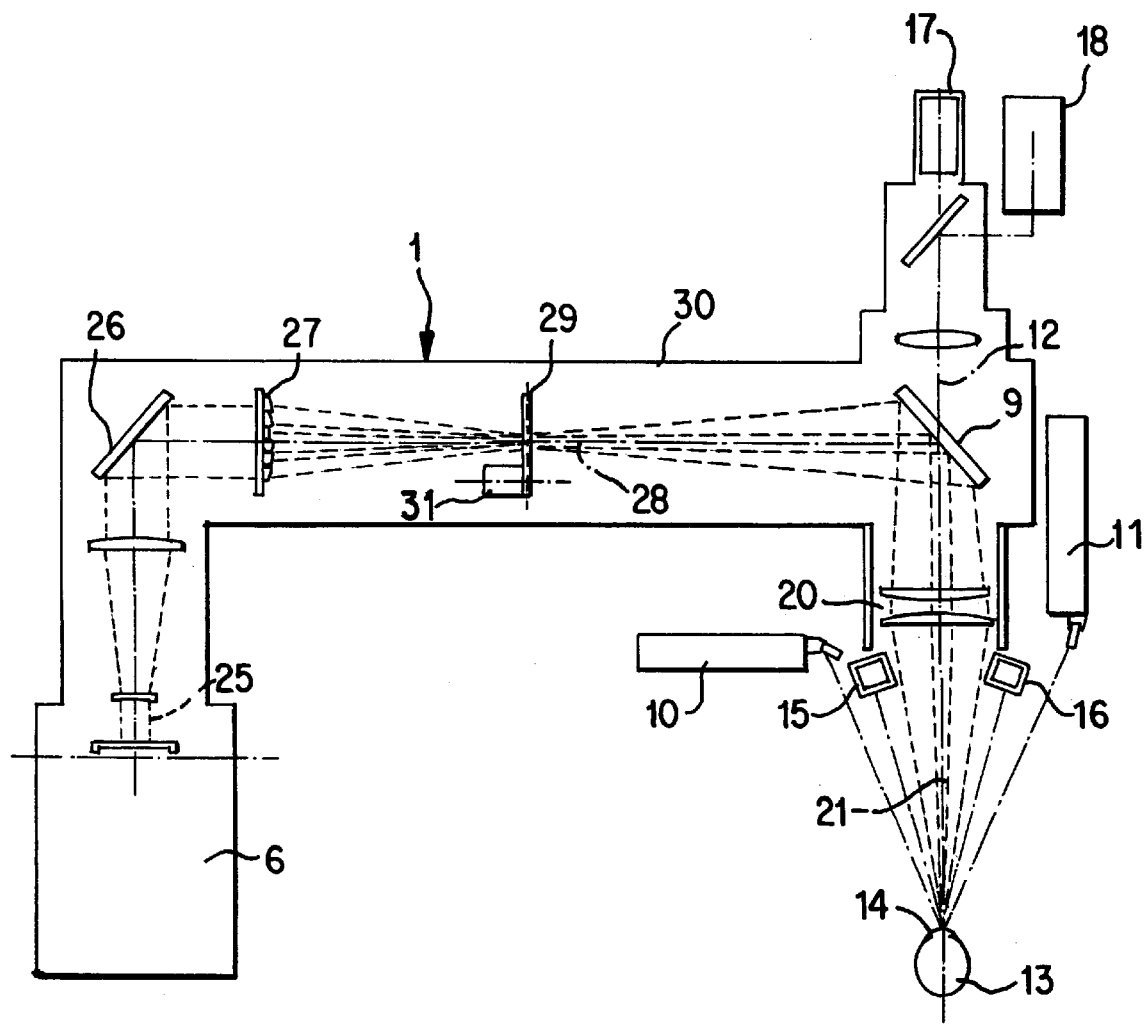
FIG. 3: in a more detailed diagrammatic representation, a total view of a device which is an embodiment example of the invention.

During treatment, the cross sectional shape of the beam spot formed on the tissue is rotated. In the embodiment example in FIG. 3, this takes place by rotating the diaphragm 29 by means of a rotation device 31. The rotation device 31 and the diaphragm 29 can be constructed as described in EPO, 651,082 A1.

In the case of the diaphragm examples of FIGS. 4 and 5, a relatively small diameter of the diaphragm aperture 19 is required in the invention [and], it is sufficient if the laser beam device 6 emits a laser beam 25 with a relatively small diameter. The homogeneous beam that is produced by the homogenizer 27 can also have a relatively small diameter together with homogeneous beam distribution or intensity at the location of the diaphragm 29.

Figure 8:
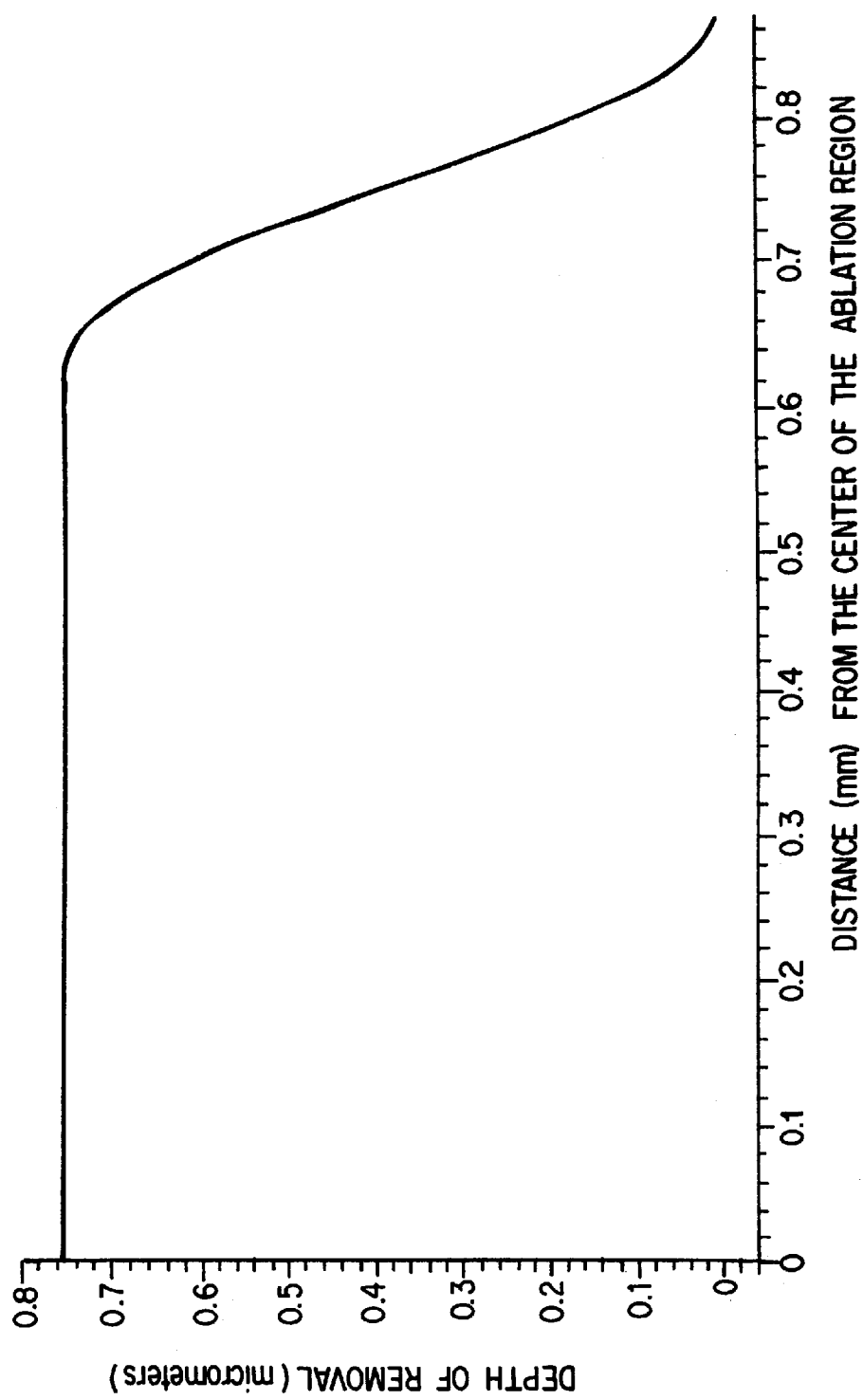
FIG. 8: a removal profile which is achieved.

As a result of rotation of the beam spot formed on the corneal tissue of the eye to be treated, a removal structure can be achieved as shown in FIG. 8. The removal structure shown in FIG. 8 is produced by pulse laser beam with a cross sectional shape of the diaphragm aperture 19 and a beam spot diameter of 1.75 mm on the surface of the tissue. A removal depth of approximately 0.75 mm was achieved with the help of three beam pulses. The removal depth is constant over a beam diameter of approximately 1.2 mm and has at the edge an angled profile course with an inflection point as, for example, is shown in FIG. 2. This removal profile permits the creation of a continuous transition at the edge of the treated region of the cornea of the eye relative to the untreated corneal tissue of the eye. In addition, one achieves a reduced depth of removal in the case of refraction correction.

During treatment, the rotated laser beam spot scans the entire surface of the tissue to be treated. Thereby, a corresponding number of laser beam pulses is brought into action depending on the removal depth to be achieved at the various parts of the tissue surface. In order to guide the laser beam spot over the tissue surface to be treated, a deflection device is provided for the laser beam 21 used for the treatment. Embodiment examples of such a beam deflection device are illustrated in FIGS. 6 and 7.

Figure 6:
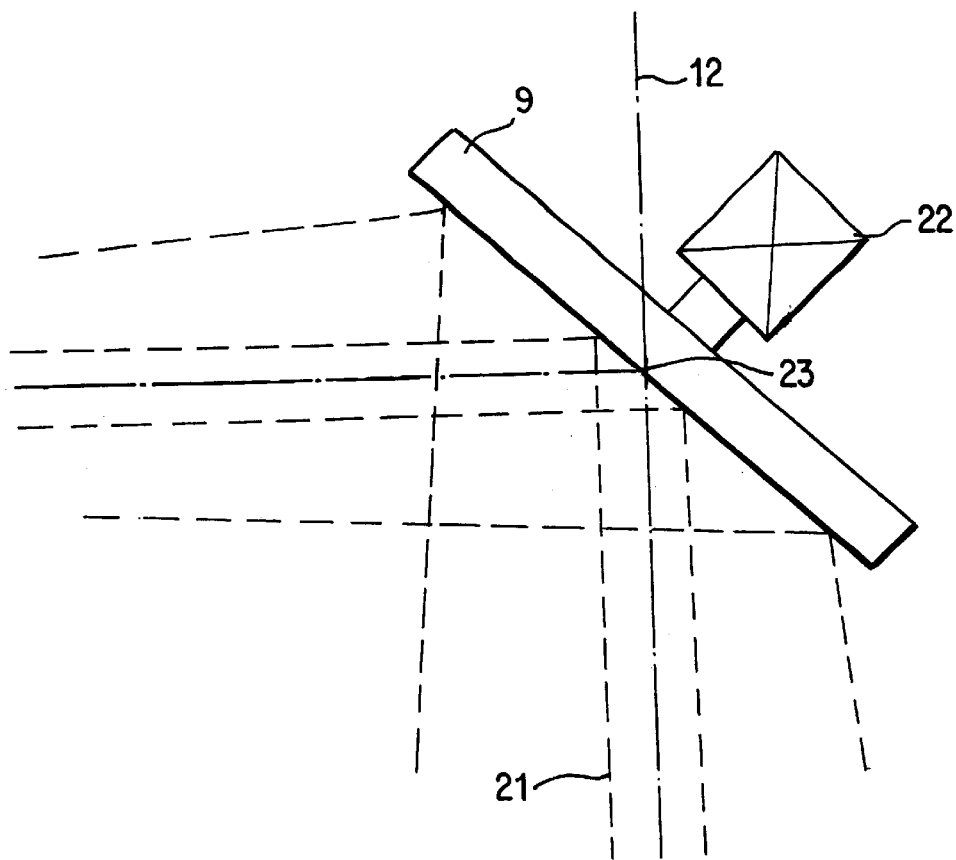
FIG. 6: an initial embodiment of a beam deflection device.

To move the beam spot in the embodiment example represented in FIG. 6, the deflection mirror 9 is moved over the tissue surface to be treated about a point of rotation 23. This point of rotation 23 is formed from the point of intersection of the fixed line 12 with the reflective surface of the deflection mirror 9 at which the laser beam 21 used for treatment is reflected. With the help of a correspondingly constructed drive device 22 and a corresponding ball joint or universal jointed suspension of the deflection mirror 9, one can achieve the desired deflection or scanning movement of the laser beam 21 used for treatment on the corneal tissue of the eye. This movement takes place about the point of rotation 23, whereby the laser beam 21 used for treatment is deflected in the desired manner relative to the fixed line 12, that remains fixed. Deflection takes place in a spatial angular range in this regard.

Figure 7:
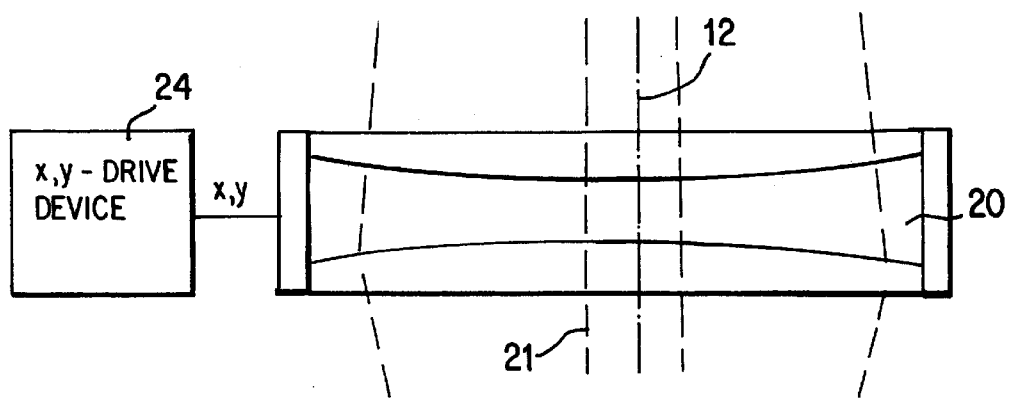
FIG. 7: a second embodiment of a beam deflection device.

In order to produce the desired deflection of the laser beam 21 that is used for treatment, in the embodiment example represented in FIG. 7, the objective lens system 20 is moved with the help of an x,y-drive device 24 in a plane that is vertical to the fixed line 12. Naturally, it is also possible to provide an additional optical deflection system with which the x,y-drive device 24 is moved in a plane that is vertical to the fixed line 12.

The two deflection devices represented in FIGS. 6 and 7 can also be used in combination with one another, especially for the correction of astigmatism. However, it is also possible to achieve astigmatism correction with one of the two deflection devices in FIGS. 3 and 4, respectively.

Instead of the diaphragm apertures that are shown in FIGS. 4 and 5, use can also be made of other shapes for the diaphragm aperture for the formation of the cross section of the laser beam 21 used for treatment. These diaphragm aperture shapes can be constructed in such a way in this connection that they are formed from several circular diaphragm apertures as shown in, for example, FIGS. 6–8 of EPO 651,802 A1. These circular diaphragm apertures with differing diameters can also be aligned in a narrow diameter—with a reduced passage aperture relative to the diaphragm in EPO 651,982 A1, centered about the center of the diaphragm or about the axis of rotation of the diaphragm. Thereby, a diaphragm aperture shape is preferred that corresponds to FIG. 6 of EP O, 651,982 A1.

Furthermore, diaphragm aperture shapes can be used as shown in FIGS. 9–14 of EPO 651,982 A1. However, the diaphragm apertures have a reduced surface area. Relative to FIG. 11, the diaphragm aperture has a 5–15% reduced aperture area.

The invention is not only usable in the radiation of the cornea of the eye, but it can also be used for the treatment of stroma tissue in the cornea of the eye after the partial or complete lifting off of the corneal lamella and replacing the lifted off corneal lamella onto the treated stroma tissue.

What is claimed is:

1. Apparatus for correction of a refraction anomaly in an eye by removal of tissue from a cornea of the eye, comprising:

a laser beam source which emits a laser beam;

a beam homogenizer through which said laser beam passes to produce a constant intensity laser beam having a constant intensity over its cross section;

a diaphragm device which produces a shaped laser beam from the constant intensity laser beam;

optical elements which direct the shaped laser beam received from the diaphragm device onto the cornea of the eye; and a control device which includes a memory in which a removal profile of beam intensity is stored, said removal profile having a concave internal radial region extending from a central beam axis to a point of inflection, which lies at about 40–60% of a radial dimension of a beam cross section starting from the central beam axis, and an outer radial region extending beyond the point of inflection with a non-concave course;

wherein data required for correction of the refraction anomaly are entered into said control device and, together with said removal profile stored in said memory, provide the shaped laser beam with a desired beam intensity profile which is transferred to the cornea for correction of the refraction anomaly.

2. Apparatus according to claim 1, wherein the beam homogenizer is aligned between the laser beam source and the optical elements, whereby the beam homogenizer produces a constant intensity distribution over a beam cross section.

3. Apparatus according to claim 1, wherein the diaphragm device forms at least one beam spot that deviates from a circular form on a tissue surface to be treated.

4. Apparatus according to claim 1, wherein the shaped laser beam which is transferred to the cornea forms a surface beam spot on a surface of the cornea that is smaller than the surface of the cornea.

5. Apparatus according to claim 1, wherein said optical elements include a deflection device by which the shaped laser beam is guided over a surface of the cornea.

6. Apparatus according to claim 1, wherein the laser beam is formed in pulses and deflection thereof takes place in synchrony with one or several laser beam pulses.

7. Apparatus according to claim 1 wherein the laser beam is deflected with respect to a fixed line along which the eye is aligned.

8. Apparatus according to claim 1, wherein the diaphragm device simultaneously forms one or several beam spots on a tissue surface to be treated.

9. Apparatus according to claim 8, wherein an aperture rim of the diaphragm device has a form of a polygon.

10. Apparatus according to claim 8, wherein an aperture region of the diaphragm device is star-shaped.

11. Apparatus according to claim 8, wherein an aperture region of the diaphragm device has a regular geometrical configuration.

12. Apparatus according to claim 8, wherein an aperture region of the diaphragm device has an irregular geometrical configuration.

13. Apparatus according to claim 8, wherein cross-sectional geometry of an aperture of the diaphragm device is formed by uneven, curving lines.

14. Apparatus according to claim 8, wherein a surface dimension of each beam spot is approximately 1/30 to 1/10 of a surface dimension of the cornea.

* * * * *